United States Patent
Lee (10) Patent No.: US 8,960,499 B2
(45) Date of Patent: Feb. 24, 2015

(54) FLUID DELIVERY APPARATUS

(76) Inventor: Freddie Eng Hwee Lee, Singapore (SG)

(*) Notice: Subject to any disclaimer, the term of this patent is extended or adjusted under 35 U.S.C. 154(b) by 0 days.

(21) Appl. No.: 14/114,103

(22) PCT Filed: Apr. 24, 2012

(86) PCT No.: PCT/SG2012/000146
§ 371 (c)(1),
(2), (4) Date: Oct. 25, 2013

(87) PCT Pub. No.: WO2012/148357
PCT Pub. Date: Nov. 1, 2012

(65) Prior Publication Data
US 2014/0048558 A1     Feb. 20, 2014

Related U.S. Application Data

(60) Provisional application No. 61/479,650, filed on Apr. 27, 2011.

(51) Int. Cl.
| | |
|---|---|
| *B65D 35/28* | (2006.01) |
| *A61M 5/148* | (2006.01) |
| *A61M 5/145* | (2006.01) |
| *B65D 83/00* | (2006.01) |

(52) U.S. Cl.
CPC ......... *B65D 83/0072* (2013.01); *A61M 5/1454* (2013.01); *A61M 5/148* (2013.01); *Y10S 128/12* (2013.01)
USPC ............. 222/95; 222/103; 222/107; 222/386; 604/135; 604/134; 604/131; 128/DIG. 12

(58) Field of Classification Search
CPC .... A61M 5/148; A61M 5/1454; B65D 35/28; B65D 83/0072; B65D 83/0055
USPC ............ 222/103, 95, 107, 386; 604/134, 135, 604/131; 128/DIG. 12, DIG. 13
See application file for complete search history.

(56) References Cited

U.S. PATENT DOCUMENTS

| | | | |
|---|---|---|---|
| 4,384,578 A * | 5/1983 | Winkler ...................... | 604/114 |
| 4,813,280 A | 3/1989 | Miller et al. | |

(Continued)

FOREIGN PATENT DOCUMENTS

| | | | | |
|---|---|---|---|---|
| DE | 44 04 395 A1 | 8/1995 | | |
| JP | 01009187 A * | 1/1989 | ............. | B65D 83/00 |

(Continued)

OTHER PUBLICATIONS

International Search Report from International Application No. PCT/SG/2012/000125 mailed Jul. 23, 2012.

*Primary Examiner* — Kevin P Shaver
*Assistant Examiner* — Nicholas J Weiss
(74) *Attorney, Agent, or Firm* — Wolf, Greenfield & Sacks, P.C.

(57) ABSTRACT

A pump apparatus that exerts a constant force on a bag of fluid to provide a uniform flow rate compared to elastomeric pumps. The apparatus comprises a first and a second block member positioned over a plate, which are moveable to define an opening to receive a wedge member attached on the plate. The block members are coupled by a resilient means that is extendable when the wedge member is urged into the opening. The extended resilient means is retractable such that the plate exerts a constant force on the bag to expel fluid in a uniform flow rate.

13 Claims, 9 Drawing Sheets

(56) References Cited

U.S. PATENT DOCUMENTS

| | | | |
|---|---|---|---|
| 4,938,079 A | * | 7/1990 | Goldberg ................... 73/861.95 |
| 5,891,096 A | | 4/1999 | Hyun et al. |
| 6,367,666 B1 | * | 4/2002 | Hou et al. .................. 222/386.5 |
| 6,948,636 B1 | | 9/2005 | Fischer et al. |
| 7,337,922 B2 | * | 3/2008 | Rake et al. ................... 222/103 |
| 7,914,500 B2 | * | 3/2011 | Gafner-Geiser et al. ..... 604/192 |
| 2004/0026448 A1 | | 2/2004 | Pichotte et al. |

FOREIGN PATENT DOCUMENTS

| | | | | |
|---|---|---|---|---|
| JP | 01037382 A | * | 2/1989 | ............. B65D 83/00 |
| WO | 2009/144726 A1 | | 12/2009 | |

\* cited by examiner

FLUID DELIVERY APPARATUS

CROSS-REFERENCE TO RELATED APPLICATIONS

This application is a national stage filing under 35 U.S.C. §371 of International Application No. PCT/SG2012/000146, filed Apr. 24, 2012, entitled FLUID DELIVERY APPARATUS, the entire content of which is incorporated by reference herein. International Application No. PCT/SG2012/000146 claims priority under 35 U.S.C. §119 (e) to U.S. Provisional Application No. 61/479,650, filed Apr. 27, 2011.

TECHNICAL FIELD

Embodiments of the invention relate to a pump apparatus for fluid delivery, in particularly for providing a constant flow rate for fluid delivery.

BACKGROUND

The advent of elastomeric pump devices has made infusion possible in non-hospital based, ambulatory settings. Typically the construction of such device consists of an elastomeric bladder that stores the energy when filled with drug of fluid. This energy that is derived from the expanded bladder pushes the fluid out via tubing when the bladder compresses. The flow rate is controlled by appropriate sized lumen of a PVC tube or orifice of a glass capillary. Such single-use devices have the advantages of convenience, safety and without the complications of electronics.

Figure 1:
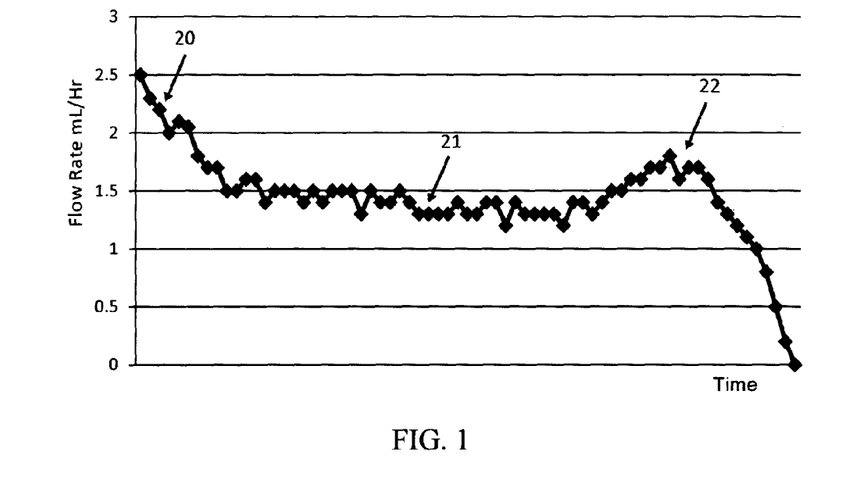
FIG. 1 is a plot diagram of a typical flow profile of fluid dispensed from an elastomeric pump.

One major drawback of elastomeric pumps is the difficulty to achieve accurate flow accuracy throughout the entire flow duration. Referring to FIG. 1, a typical flow profile (i.e. flow rate vs. time) of an elastomeric pump shows that the flow rate of fluid from such a pump is not constant during the flow duration because the pressure exerted on the fluid in the pump is not constant due to the inherent characteristics of such pumps. Flow begins with an inherent initial spike 20, continues with a trough shaped phase 21 having a lower flow rate, and finishes with a slight second spike 22. While the troughs and peaks of such a profile may be averaged to provide a sufficient flow rate, in some cases, such as for the delivery of toxic medication or when a narrow therapeutic range is required, the initial spike may result in an overdose or another undesirable situation. To overcome this, some manufacturers recommend that such pumps be left aside for an initial period, presumably for the elastomer to relax before infusion starts.

Another drawback of elastomeric pumps is that the energy stored in the bladder is dependent on the fluid fill volume. Depending on the geometry and intrinsic characteristics of the material used, variations in fill volume may result in changes in flow rate to a varying extent. This dependency of flow rate and flow duration on fill volume is evident in the relatively fixed fill volume that is specified for any such pump. Only small variations in fill volume are permitted if the specified flow rate is to be attained.

The present invention addresses the above issues by making possible infusion delivery of fluid with a constant flow accuracy that is unaffected by the non-uniform pressure exerted by the expanded bladder in elastomeric devices. This non-uniform pressure is due to the changing fill state of the conventional bladder as its content is delivered and also to some extent on the duration the content remains in the bladder which could affect its elasticity. As pressure generated in the present invention is independent of the filled state and that there is no impact of the duration during which the content remains in the device, the performance characteristics of the device can be optimized relatively easily at its design stage.

SUMMARY

According to one embodiment of the invention, an apparatus for fluid delivery from a flexible container is provided. The apparatus has a bottom casing and a top casing attached to the bottom casing. A wedge member is disposed between the bottom casing and the top casing. The wedge member and the bottom casing form a space to receive the flexible container therein. A first block member and a second block member are arranged between the wedge member and the top casing. A narrow end of the wedge member is disposed between the first and second block members. A resilient means is coupled to at least one of the first and second block members. The resilient means causes the first and second block members to move towards each other by which the wedge member moves towards the bottom casing to squeeze the fluid out of the flexible container.

According to one embodiment of the invention, a pump apparatus for fluid delivery comprises a plate arranged over a bottom casing. A wedge member extends from the plate. At least a first and a second block member are arranged over the plate and are moveable to define at least an opening for receiving the wedge member. A resilient means couples the first and second block member. An increase in displacement between the plate and bottom casing urges or pushes the wedge member into the opening to displace the resilient means into an extended position. When in the extended position, the resilient means exerts a substantially constant compressive force on a bag of fluid disposed between the plate and bottom casing.

The force exerted on a filled bag enclosed in the pump apparatus is relatively constant, resulting in a more uniform flow rate compared to elastomeric pumps. Furthermore, as this force is constant throughout the filled state of the bag, such a pump apparatus can be constructed to accept varying fill volumes without affecting the flow rate. The bag that contains the fluid or medication is made from materials already widely used in the medical field, with proven non-adverse compatibility properties.

According to another embodiment of the invention, there is provided a kit of parts for assembling a pump apparatus for fluid delivery. The kits of parts comprises a bottom casing, a plate having a first and a second surface, a wedge member attachable to the second surface. A resilient means for coupling at least a first and a second block member, the first and second block members moveable to define at least an opening for receiving the wedge member. A top casing is attachable to the bottom casing, the top casing for supporting the first and second block members. The pump apparatus can be assembled on site.

BRIEF DESCRIPTION OF THE DRAWINGS

Embodiments of the invention will be readily understood by the following detailed description in conjunction with the accompanying drawings.

DETAILED DESCRIPTION

In the following description, numerous specific details are set forth in order to provide a thorough understanding of various illustrative embodiments of the invention. It will be understood, however, to one skilled in the art, that embodiments of the invention may be practiced without some or all of these specific details. In other instances, well known fluid delivery or infusion processes and mechanisms have not been described in detail in order not to necessarily obscure pertinent aspects of embodiments being described.

Embodiments of the invention relate to a pump apparatus comprising a bottom casing and a plate arranged over the bottom casing. A wedge member extends from the plate. At least a first and a second block member are arranged over the plate and are moveable to define at least an opening for receiving the wedge member. A top casing is removably attached to the bottom casing for supporting the first and second block members. Furthermore, a resilient means couples the first and second block member, where an increase in displacement between the plate and bottom casing urges or pushes the wedge member into the opening to displace the resilient means into an extended position. When in the extended position, the resilient means exerts a substantially constant compressive force on and to squeezes a flexible fluid container disposed between the plate and bottom casing.

Figure 9A:
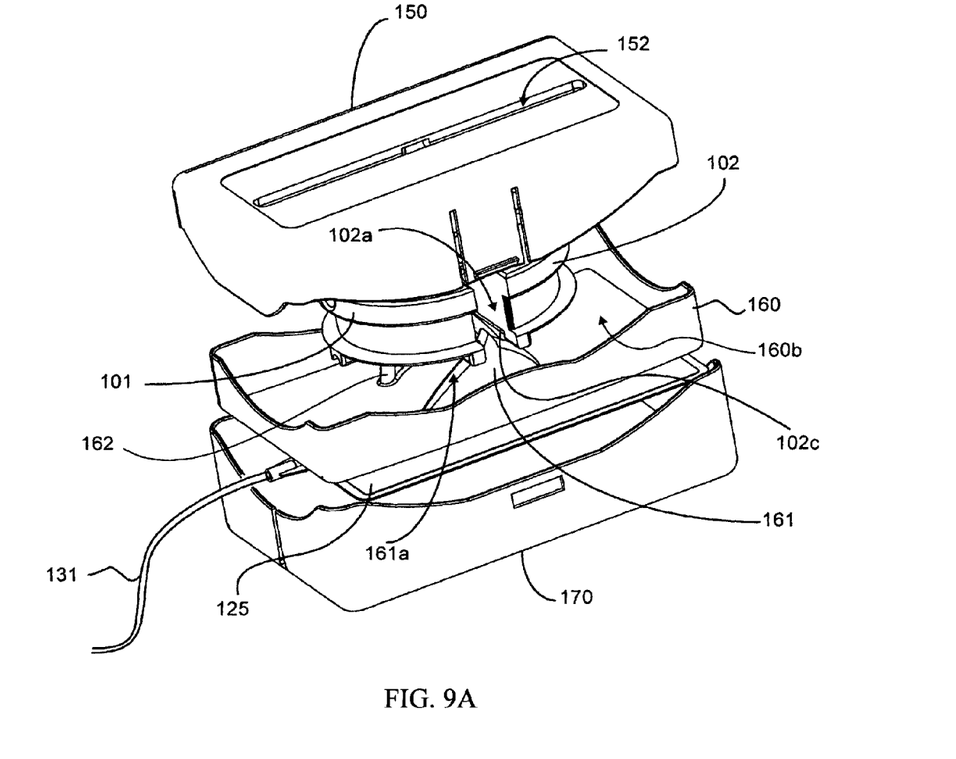
FIG. 9A is an unassembled perspective view of the pump apparatus in accordance with one embodiment of the invention.
Figure 10:
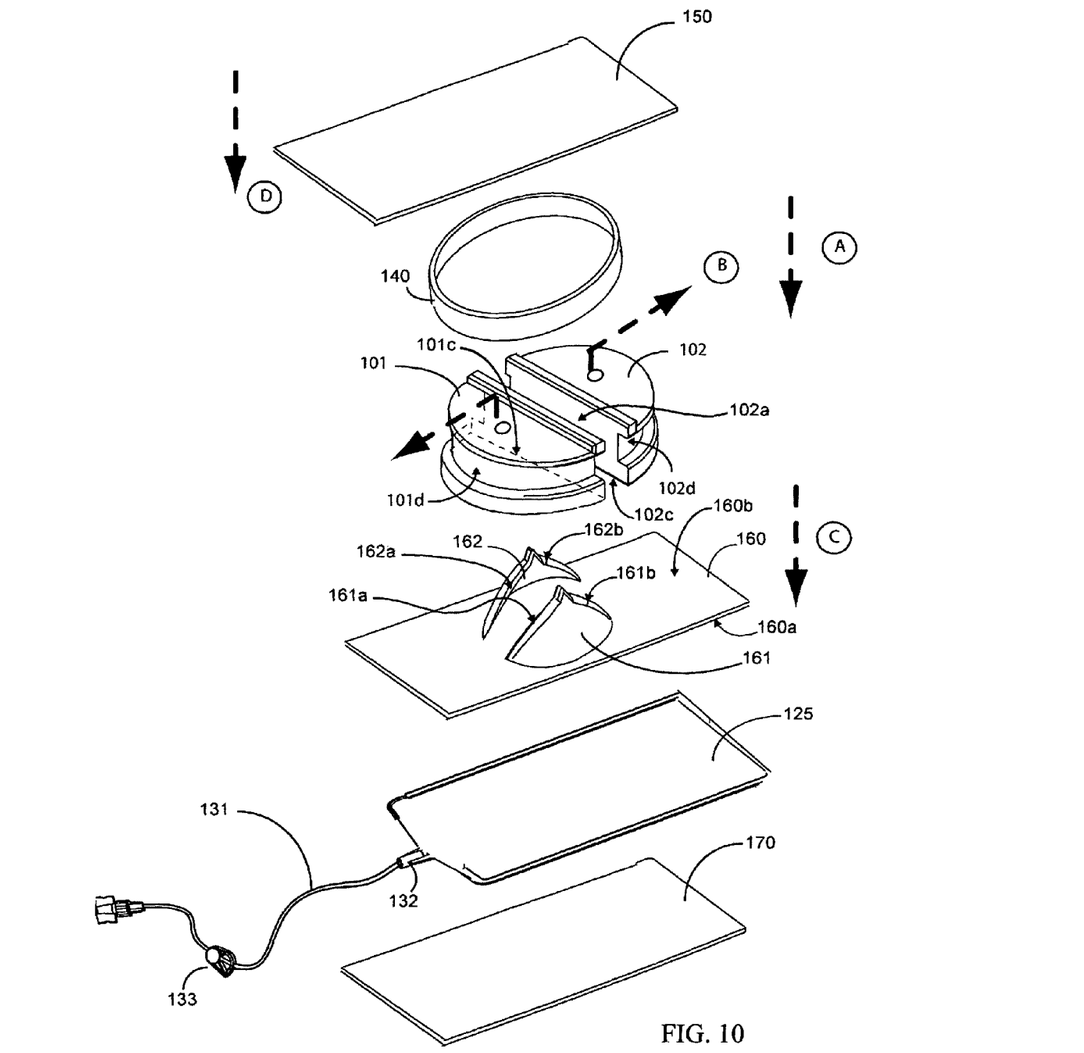
FIG. 10 is an unassembled perspective view of the pump apparatus in accordance with another embodiment of the invention.

Referring to FIG. 9A, the pump apparatus comprises a top casing 150 attachable to a bottom casing 170, and a plate 160 between the top and bottom casings 150, 170. In one embodiment, the top casing 150 and bottom casing 170 are welded or bonded together (e.g. using solvent or glue), and the plate 160 is moveable between the top and bottom casings 150, 170. In another embodiment, the top casing 150 and bottom casing 170 may encompass other forms, such as plates (FIG. 10) that are secured to each other by fasteners or rods. A flexible container, e.g. a bag 125 can be built or inserted between the bottom casing 170 and the plate 160, which requires filling of the bag 125 prior to use. The filling of the bag 125 is done by means of a syringe or commercially available repeater pumps. Alternatively, a pre-filled bag is placed between the bottom casing 170 and plate 160, which are subsequently attached. Yet in another embodiment, the plate 160 and the top and bottom casings 150, 170 can be supplied as an integrated sub-assembly (FIG. 10). These components could be assembled on-site, for example in a pharmacy, by means of a jig such that the pre-filled bag could deliver infusion at a constant flow rate when a tubing with an appropriate orifice is attached, or pre-attached.

The pump apparatus exerts relatively constant pressure on the contents of the bag 125. The bag 125 is usually made of PVC sheets or other elastic/pliable polymer commonly used in the medical field to store fluid or medication. In one embodiment, the bag 125 has tubing 131 pre-attached, as well as in-line appropriate sized lumen of orifice to control the flow rate. In other embodiments, the tubing 131 could be a separate entity and attached by a connector or spike to the bag 125 prior to infusion.

In one embodiment, the fluid to be delivered by the pump apparatus is administered or injected into the bag 125 via a filling port 132 in-line with tubing 131 (FIG. 10). For example, the filling port 132 can be directly attached to one edge of the bag 125. This can be done manually with a filling device like a syringe or any automated filling machines widely available. The fluid is retained in the bag 125 by an anti-siphon valve or equivalent one-way valves, which typically is incorporated in the filling port 132.

Figure 9B:
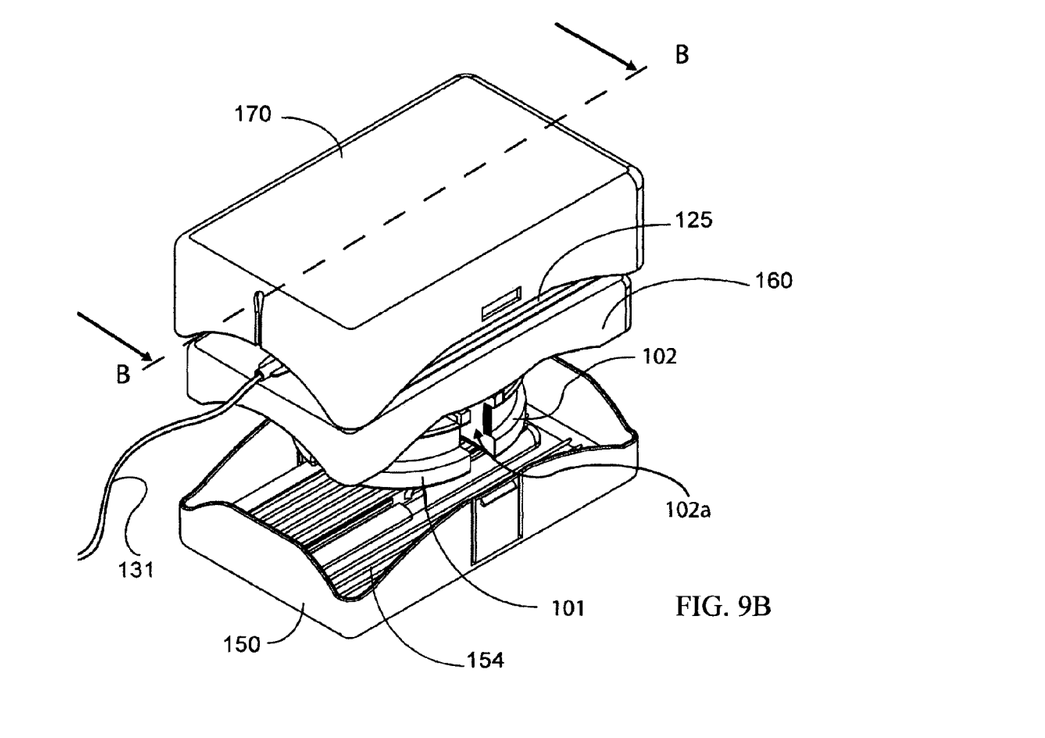
FIG. 9B is an alternative view of the pump apparatus illustrated in FIG. 9A.

In an embodiment of the invention, the pump apparatus comprises at least a first and a second block member 101 and 102 that are coupled by a resilient means (FIG. 10). In one embodiment, the resilient means comprises an elastic band 140 binding first and second block members 101 and 102 together. Elastic band 140 may be made of rubber or any stretchable polymer that sits snugly in the grooves 101d and 102d of the respective block members 101 and 102. The objective of these block members 101, 102 is to stretch or extend the elastic band 140 to store a potential energy in elastic band 140, when the contact surfaces 101a, 102a of these block members 101, 102 are displaced from one another. The block members 101, 102 are further arranged in such a configuration that they will have the tendency to assume their original or home position when the stretched or extended elastic band 140 is free to retract to release the potential energy. In essence the elastic potential energy stored in stretched elastic band 140 is transferred to the block members 101, 102 potential energy relative to its home or original position. For clarity purposes, the elastic band 140 is not illustrated in FIGS. 9A, 9B and 9C.

In one embodiment, the block members 101 and 102 are semi-circular cylinders (FIG. 10). In other embodiments, the block members 101 and 102 can be of other geometrical shapes and may be of any number. In the home/original position, the two block members 101 and 102 would have their respective contact surfaces 101a and 102a in contact or in closest proximity facing each other (e.g. FIG. 8). It can be appreciated that in other embodiments with more block members or with block members of different geometrical shape, the number and shape of such contact surfaces would vary.

In one embodiment, the plate 160 has a surface 160a facing the bottom casing 170, and an opposite surface 160b on which two wedge members 161, 162 are extended. The wedge members 161, 162 are moveable in a vertical direction in a piston or plunger-like manner when the block members 101 and 102 are displaced in a horizontal or lateral direction. In one embodiment, the wedge member 161 has contact edges 161a and 161b, which form a tapered profile with a tip pointing towards the block members 101, 102 and top casing. Similarly, wedge member 162 has contact edges 162a, and 162b that forms similar tapered profile as wedge member 161. The contact edges 161b and 162b of the respective wedge members 161 and 162 are contactable with the contact edge 102c of block member 102. On the other side, contact edges 161a and 162a of wedge members 161 and 162 are contactable with the contact edge 101c of block member 101. It can be appreciated that the pump apparatus may include one or more wedge members.

Figure 9C:
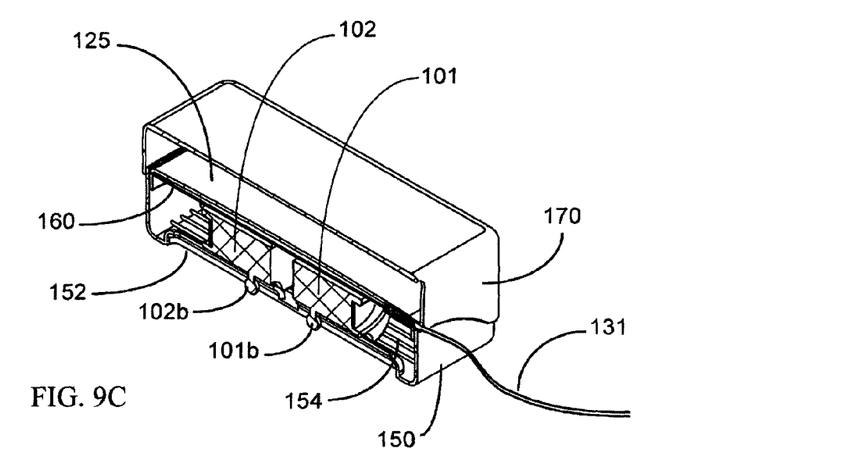
FIG. 9C is a cross-sectional view of the pump apparatus taken along the line B-B in FIG. 9B.

Referring to FIGS. 9A and 9C, the top casing 150 comprises a groove or slot 152 that is engageable to a projection, e.g. a knob member 101b/102b on each block member 101/102 to guide the movement of first and second block members, and to allow sturdy yet smooth movement of the block members 101 and 102. These knob members 101b and 102b could also be used as approximate volume indicators, as they move outwards when the bag is filled and move inwards when the bag empties. In one embodiment, the inner surface of top casing 150 may have ribs 154 or is corrugated (FIGS. 9B and 9C) to reduce the contact area between the moving block members 101 and 102 with itself, which helps to reduce friction.

Figure 6:
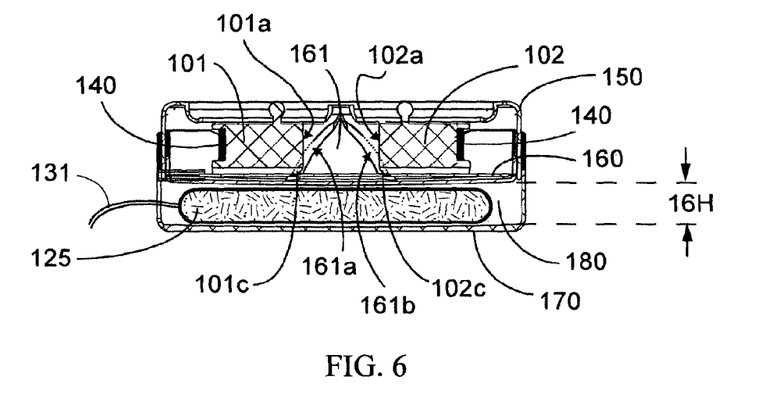
FIG. 6 is a cross-sectional view of the pump apparatus with a bag in its undispensed state.
Figure 7:
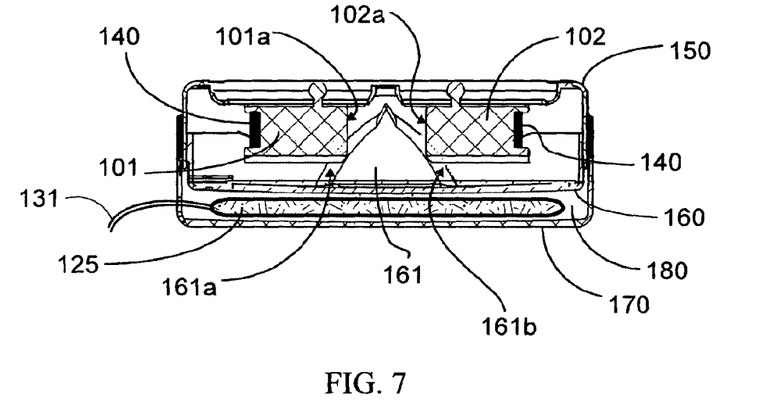
FIG. 7 is a cross-sectional view of the pump apparatus during a certain state of the dispensation cycle.
Figure 8:
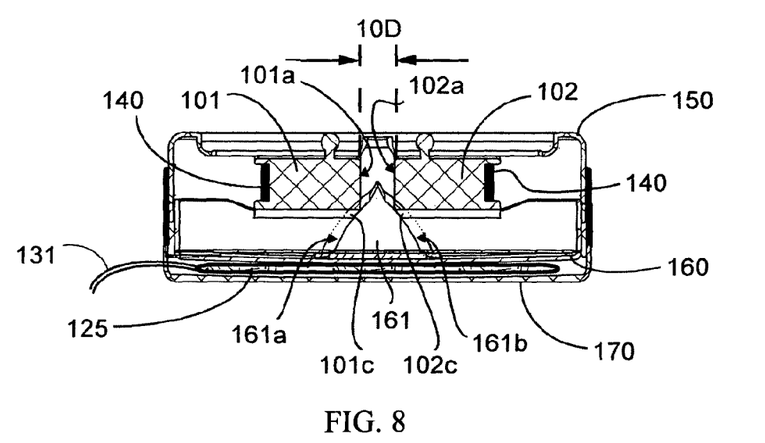
FIG. 8 is a cross-sectional view of the pump apparatus with the fluid fully dispensed from the bag.

Referring to FIGS. 6, 7, and 8, the plate 160 on which the wedge members 161 and 162 are rigidly secured is in continuous contact to one surface of the bag 125. The top casing 150 is attached to the bottom casing 170, wherein the top casing 150 supports block members 101, 102 between the top casing 150 and the wedge members 161, 162. Any displacement of the block members 101, 102 in the horizontal direction will consequently cause a vertical displacement/movement of the wedge members 161, 162 and the plate 160.

In FIG. 6, the bag 125 is in its maximum filled state or substantially filled with fluid and the elastic band 140 is in a stretched or extended position. As the pump apparatus provides relatively constant force on the bag 125 at varying fill volumes, the user has the flexibility of using the pump apparatus for a wide range of fill volume without significant effect on the flow rate. To start infusion, a clamp 133 (see FIG. 10) or valve on the tubing 131 is released to allow fluid to flow out of the bag 125, which cause the bag 125 to compress or reduce in volume. The stretched elastic band 140 then retracts to release the potential energy, which causes the plate 160 to exert a compressive force on the bag 125, thus expelling the fluid (FIGS. 7 and 8). When the fluid is totally or substantially expelled from the bag 125 (FIG. 8), the elastic band 140 is in a relaxed state/position or less stretched than its extended position in FIG. 6.

In one embodiment, the tip or narrow end of the wedge members 161, 162 are aligned at the point of contact of the two block members 101, 102 such that the vertical movement of wedge members 161, 162 (towards the top casing 150) push the block members 101, 102 apart, resulting in the two block members 101, 102 moving away from each other, hence creating or widening a rift-like space or opening between the block members 101, 102. This movement of the contact edges 101c and 102c of block members 101 and 102 respectively away from each other is attributed to the contour of the wedge members 161, 162 at its point of contact with the block members 101 and 102. The contact edges 161a, 161b and 162a, 162b of the wedge members 161 and 162 are such that the effective distance or rift/opening created between the block contact edges 101c and 102c increases as the wedge members 161, 162 moves further downwards. For example in FIG. 8, the plate 160 is in a relatively higher vertical position when compared to its position in FIG. 6. It follows that in FIG. 6, the rift or opening created between the contact surfaces 101a and 102a of respective block members 101 and 102 is greater than the opening in FIG. 8. The position of the plate 160 in FIG. 6 would correspond to a position when the elastic bag 125 that is filled occupies the void or space 180 between the plate 160 and the bottom casing 170.

From FIG. 6, the plate 160 and the wedge members 161 and 162 move upwards in a vertical direction as fluid in the filled elastic bag 125 is totally emptied as shown in FIG. 8. In FIG. 7, the plate 160 and the wedge members 161 and 162 are in one of the possible positions in a dispensation cycle when fluid from the elastic bag 125 is being released.

In the case where the bag 125 is empty or substantially empty (e.g. FIG. 8), the elastic band 140 is in a relax/unstretched position or in a slightly stretched position. When the bag 125 is injected with fluid, its contact surface with plate 160 pushes the plate and the wedge members 161, 162 downwards (or towards the top casing 150). The adjacent surface of the bag 125 is in contact with the inner surface of the bottom casing 170. The rift between block members 101 and 102 increases, causing the elastic band 140 to stretch into a relatively more extended position (FIG. 6 or FIG. 7).

Throughout the different positions of the wedge members 161 and 162 relative to the block members 101 and 102, the force that causes the flow of fluid from the bag 125 is derived from the tendency of the plate 160 to move vertically towards the plane formed by the surface of the bag 125 as the block members 101 and 102 retracts to its home position (for example FIG. 8). The stretched elastic band 140 (at FIG. 6 or FIG. 7) will produce a lateral force that causes the two block members 101 and 102 to return to its home position or move towards each other (e.g. FIG. 8). As a result, there is a force that acts at the point or points of contact between the block members 101, 102 and the wedge members 161, 162 in a generally horizontal direction.

In essence the block members 101, 102 and the wedge members 161, 162 function in a manner that transforms direction of the force generated by the stretched elastic band 140 from a horizontal plane to another perpendicular to it (i.e. vertical plane). The resulting vertical force is equivalent to a compressive force exerted by the plate 160 on the bag 125 that expels the fluid. The geometry of the wedge members 161, 162 at their points of contact with the two block members 101, 102 is used in determining the extent of the lateral displacement of the block members 101, 102 relative to the vertical displacement of the wedge members 161 and 162.

Figure 4A:
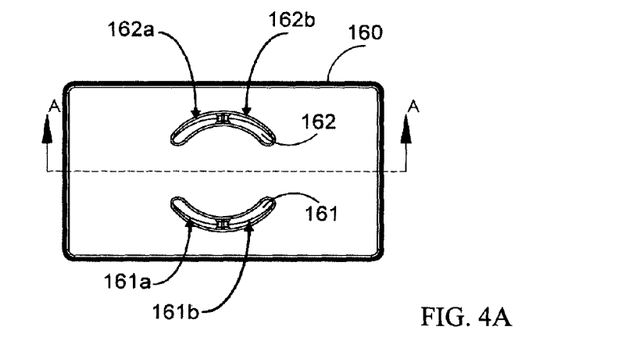
FIG. 4A is a plan view of the plate and wedge members in accordance with one embodiment of the invention.
Figure 4B:
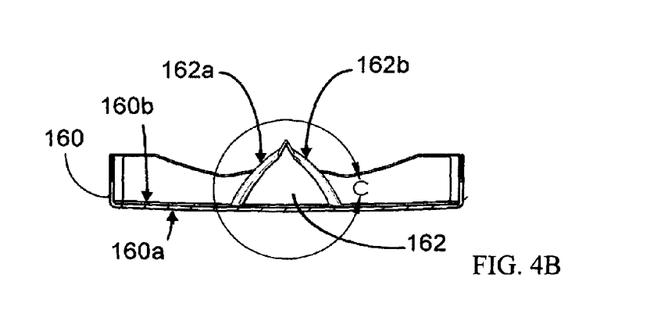
FIG. 4B illustrates the cross-sectional view of the plate taken along the line A-A in FIG. 4A.
Figure 4C:
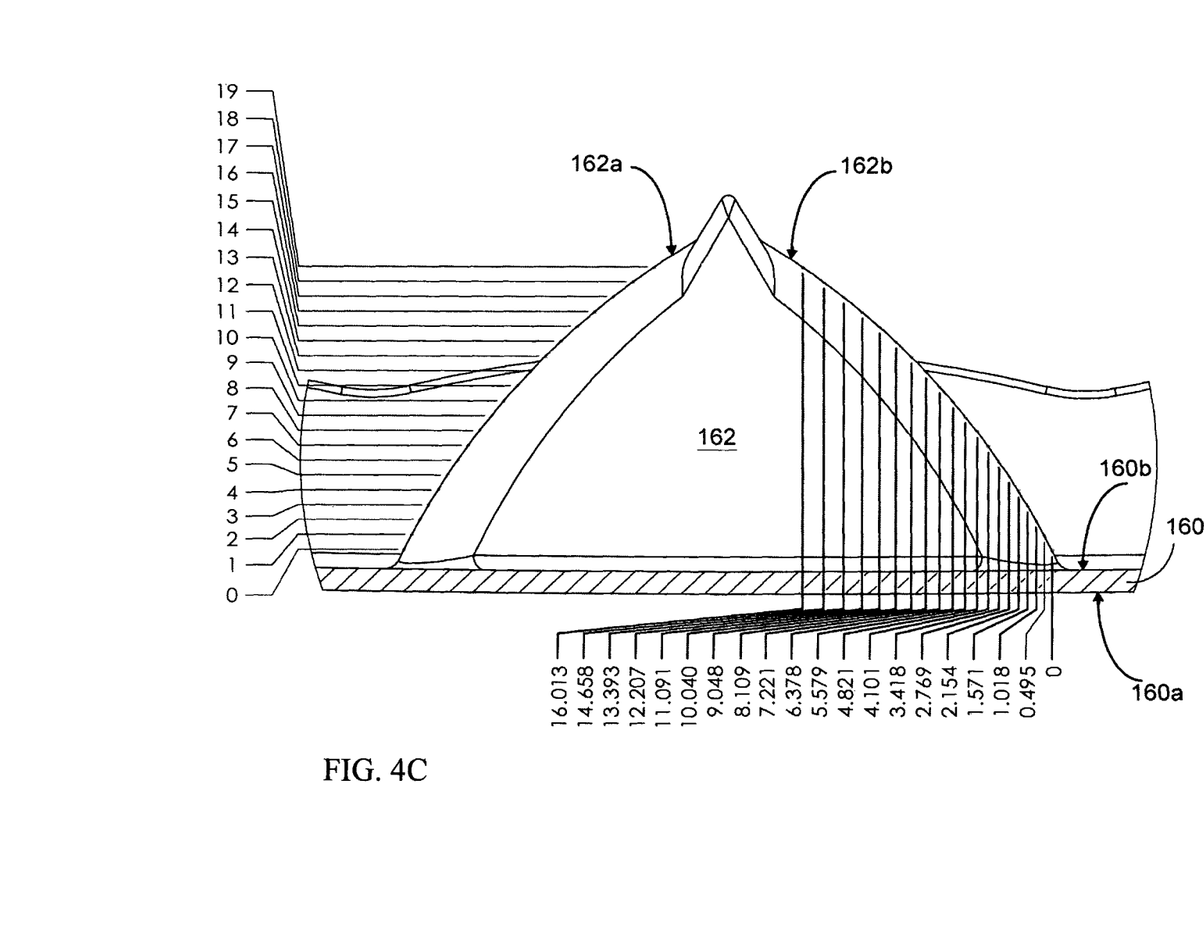
FIG. 4C is a close-up view of the wedge member show in FIG. 4B.

FIG. 4A shows a plan view of the wedge members 161, 162 on the plate 160. Wedge members 161, 162 are either attachable to the plate 160 or formed as an integral part of the plate 160. FIG. 4B illustrates the cross-sectional view of the plate 160 taken along the line A-A in FIG. 4A. Referring to FIG. 4C, the contour or profile of the contact edges 162a and 162b of the wedge member 162 determines the angle of incidence of the lateral force acting on it. This angle transforms the lateral force from the stretched elastic band 140 to an effective vertical force that acts towards the plate 160.

Figure 5A:
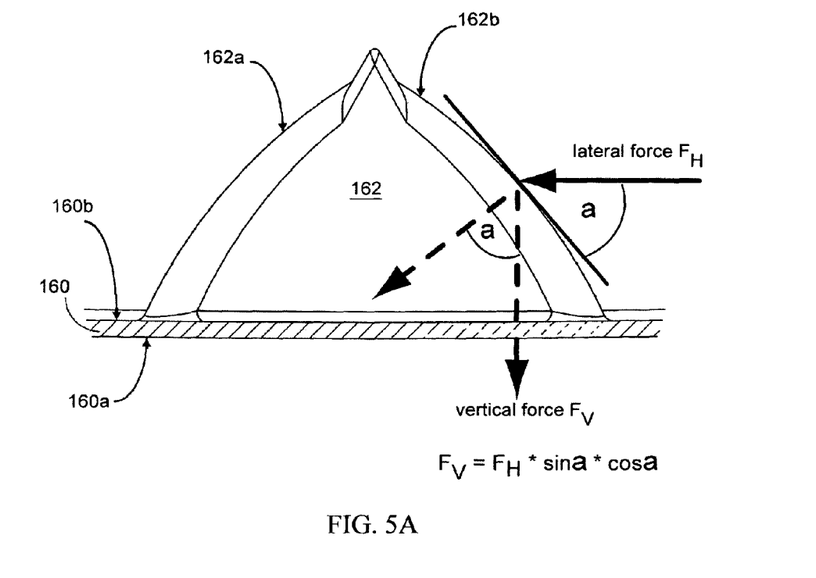
FIG. 5A illustrates the effect of the wedge member in transforming lateral force acting on it to the effective vertical force.

FIG. 5A shows the lateral force exerted on the contact edge 162b of the wedge member 162 due to the contact with the contact edge 102c of the block member 102, resulting in an angle of incidence (a). The vertical force ($F_V$) resulting from the lateral/horizontal force ($F_H$) can be defined as $F_V = F_H * \sin(a) * \cos(a)$. The angle of incidence of the force acting on the wedge member 162 varies due to its contour or profile of the contact edge 162b. Also, the lateral force acting on the wedge member 162 varies as the elastic band 140 is stretched. Referring to Table 1 and FIG. 5B, a table and a plot diagram shows the factor of transformation (sin (a)*cos (a)) at each point of the horizontal displacement of the block members 101, 102.

Further referring to FIG. 4C, FIG. 6 and FIG. 8, the relative lateral displacement 10D of the blocks 101 and 102 is shown as a function of the vertical displacement 16H of the plate 160. The range of numbers 0 to 16.013 (millimeters) represents lateral displacement while the range of numbers 0 to 19 (millimeters) represents vertical displacement. For example, lateral displacement of 0 to 0.495 mm corresponds to a vertical displacement of about 0 to 1 mm. The distance or vertical displacement 16H changes as the contact edges 161a and 162a of the respective wedge members 161 and 162 slide along the contact edge 101c of block member 101, and contact edges 161b and 162b slide along contact edge 102c of block member 102 when the elastic band 30 retracts to its un-stretched state or extends to its stretched state. With the appropriate geometry of the profile formed by contact edges 161a/161b and 162a/162b, the required change in vertical displacement 16H with any incremental change in lateral displacement 10D can be designed or adjusted accordingly.

Figure 3A:
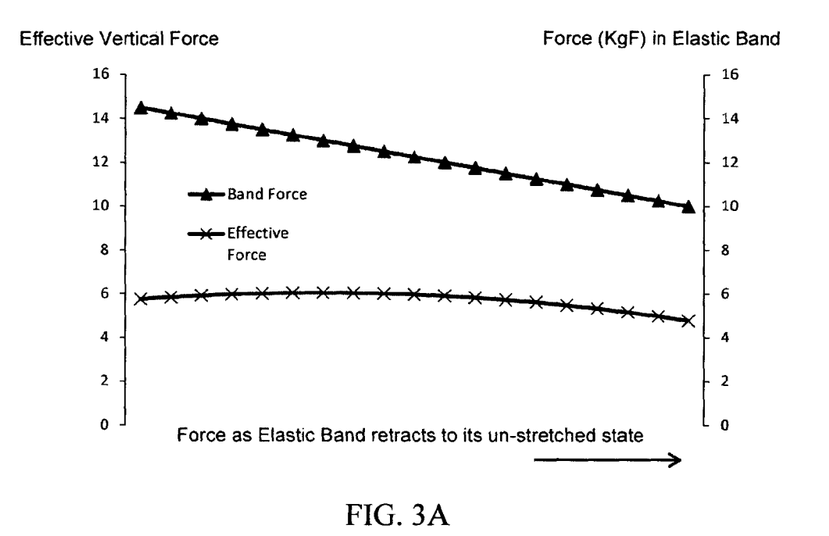
FIG. 3A is a plot diagram of the lateral force exerted by the elastic band as it retracts and causes the displacement of the wedge member in a vertical direction.
Figure 3B:
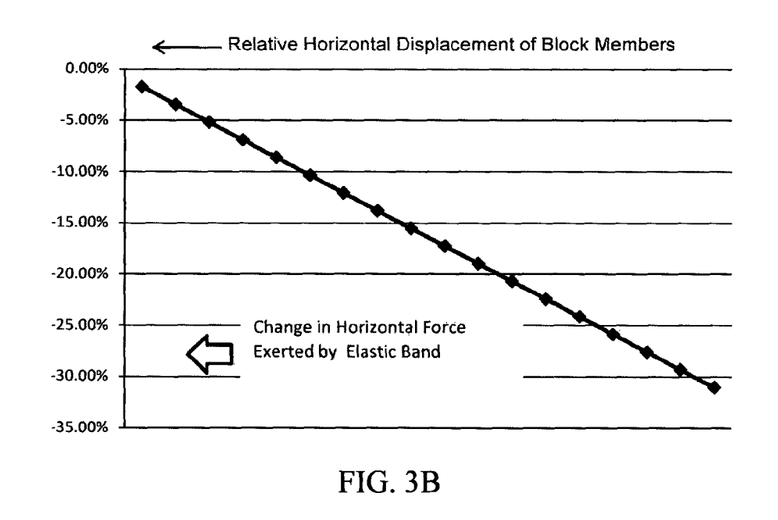
FIG. 3B is a plot diagram of the percentage change in the lateral force exerted by the elastic band as fluid in the bag is dispensed.
Figure 3C:
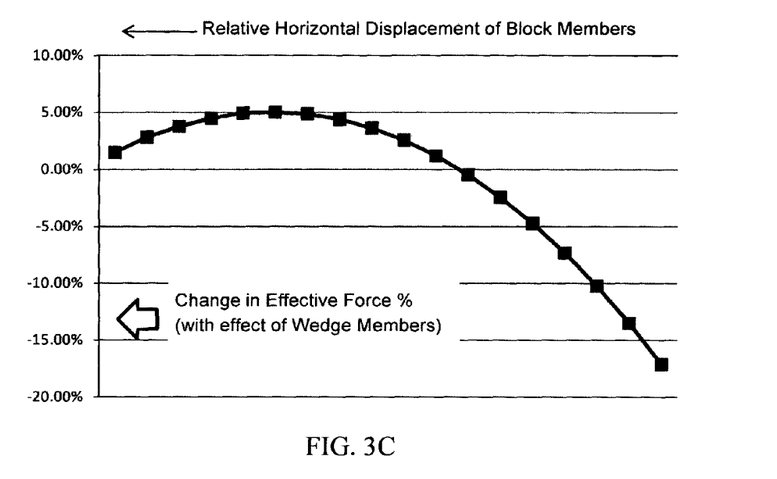
FIG. 3C is a plot of the percentage change in the effective vertical force acting on the bag as fluid is dispensed.

The lateral displacement 10D or movement of the two block members 101, 102 will cause the elastic band 140 to be stretched—the more the displacement the greater is the force exerted on the points of contact between the wedge members 161, 162 and the block members 101, 102. FIG. 3A is a plot diagram of the lateral force exerted by the elastic band 140 as it retracts and cause the displacement of the wedge members 161, 162 in a vertical direction. The corresponding effective vertical force transformed by the wedge members 161, 162 is also shown. FIG. 3B is a plot diagram of the percentage change in the horizontal or lateral force exerted by the elastic band 140 as fluid in the bag 125 is dispensed. During the dispensation cycle, the block members 161, 162 coupled by the elastic band 140 move closer towards each other. FIG. 3C is a plot diagram of the percentage change in the effective vertical force acting on the bag 125 as fluid is dispensed.

Figure 5B:
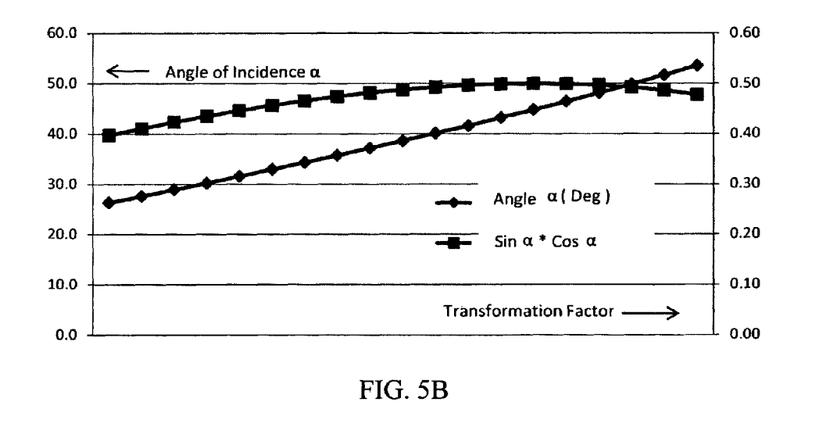
FIG. 5B is a plot diagram of the transformation factor and angle of incidence.

By combining the effects of variables of force shown in FIGS. 3A-3C and the transforming effects as shown in Table 1 and FIG. 5B, the required change in force (in this instance a constant or no change) can be derived from the design of the contact edges 161a/161b and 162a/162b and the appropriate selection of elastic band 140.

Referring to FIG. 3A, the change in the vertical force acting on the bag 125 is plotted against the change in the horizontal displacement 10D of the block members 101, 102. In this instance this vertical force changes by approximately 18%, much smaller than the 30% change in the horizontal force exerted by the elastic band 140. This is synonymous to achieving a constant force exerted by the plate 160 on a filled bag as the vertical displacement 16H changes.

TABLE 1

| Angle α(Degree) | sin α* cos α |
|---|---|
| 26.3 | 0.40 |
| 27.6 | 0.41 |
| 28.9 | 0.42 |
| 30.2 | 0.44 |
| 31.6 | 0.45 |
| 33.0 | 0.46 |
| 34.3 | 0.47 |
| 35.7 | 0.47 |
| 37.2 | 0.48 |
| 38.6 | 0.49 |
| 40.1 | 0.49 |
| 41.6 | 0.50 |

TABLE 1-continued

| Angle α(Degree) | sin α* cos α |
|---|---|
| 43.2 | 0.50 |
| 44.8 | 0.50 |
| 46.4 | 0.50 |
| 48.1 | 0.50 |
| 49.9 | 0.49 |
| 51.7 | 0.49 |
| 53.6 | 0.49 |

In one embodiment, the contact edges 161a, 161b and 162a, 162b of wedges 161 and 162 are curvilinear such that the surface encompassed by the said edges and the base of the respective wedge members 161, 162 is curved (FIG. 10). Such a structure ensures that as the wedge members 161 and 162 displace/move in a vertical direction as a result of the block members 101 and 102 moving away from or towards each other, both the contact points on the contact edge 161a, 161b, 162a, 162b of the wedge members 161a and 162a and the respective contact edges 101c and 102c of the block members change continuously. In other words, there are no points of contact on either wedge members 161, 162 or the edges of blocks 101 and 102 that remain unchanged as the distance (vertical displacement) 16H changes. This preserves the patency of the points of contact better against wear caused by friction as the wedge members 161, 162 are displaced while forming the rift/opening between block members 101 and 102.

Figure 2:
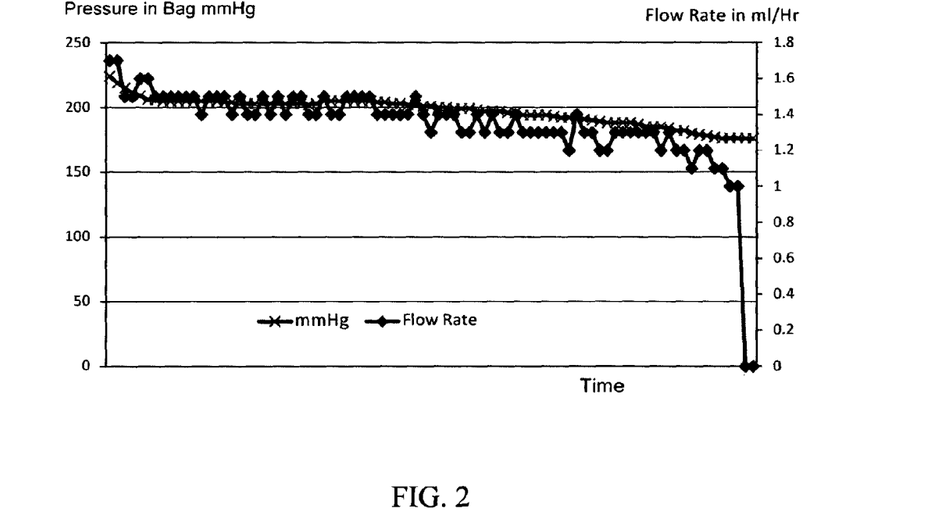
FIG. 2 is a plot diagram of a flow profile of fluid dispensed from the pump apparatus in accordance with one embodiment of the invention.

The change in gradient of the contour or profile of the wedge members 161, 162 at the effective point of contact with the block members 101, 102 is predetermined to give the necessary incremental lateral displacement of the block members 101, 102 as the wedge members move in a vertical direction so that this displacement in acting together with the stretched state of the elastic band 140 will result in the intended constant vertical force on the plate 160 as shown in FIG. 2. The pressure exerted on the fluid contained in the bag 125 is significantly more linear.

It can be appreciated that in other embodiments, the wedge members 161, 162 can be flat, tubular or cylindrical with the necessary variable tangential gradient at its edge (161a, 161b, 162a, 162b) that is in contact with the block members 101, 102.

In an embodiment of the invention, the pump apparatus provides fixed flow rates, or variable flow rates when a flow controller or regulator is attached to the bag 125 it is installed with. In either case, the user will have the flexibility of filling the pump apparatus with a wide range of fill volume, which is currently not available.

In other embodiments, the flow control tubing can be supplied separately, offering the user further flexibility in managing the inventory of such single-use pumps. In yet another embodiment, the pump apparatus could be equipped with an end of infusion alarm by allowing the contact surfaces of the plate 160 and bottom casing 170 to be the effective contact that closes an electric circuit (e.g. at the position shown in FIG. 8). The bag containing fluid can be installed empty inside the pump apparatus, or the pump apparatus could be offered in a container shaped construction with two halves of the housing (e.g. casings 150 and 170) being pressed together to enclose a bag already filled.

As the pump apparatus works by exerting force on the contents of the bag 125, there is no requirement in transferring medication into the apparatus itself. Issues related to contamination or ensuring closed system handling of medication is minimized. The pump apparatus offers maximum utility in providing a more accurate flow compared to currently available mechanical self-powered pumps, allowing fill volume to be changed without affecting desired flow rate, providing total ambulatory benefits as no batteries or electric source is needed, allowing reliability in manufacturing due to minimal moving parts and provides economical costs of manufacture.

It is apparent to those skilled in the art that the applications for the pump apparatus with constant flow could be wide and encompassing. Some of the alternative embodiments are an empty bag within the pump apparatus, filled bag to be placed inside the pump apparatus, and also the sub-assembly that could be assembled on site with vendor supplied prefilled bags, with the aid of customized jigs. FIG. 10 illustrates one possible sub-assembly configuration with assembly steps indicated by A to D. At step A, the elastic band 140 is positioned onto the block members 101, 102 before moving the block members 101, 102 apart (step B) such that the elastic band 140 sits in the grooves 101d, 102d of the block members 101, 102. Then the block members 101, 102 with elastic band 140 is arranged over the wedge members 161, 162 (step C) before the top casing is attached to the bottom casing 170 (step D). The sub-assembly option offers potential of using prefilled bags that eliminates contamination issues during filling and the use of pump apparatus as disposable single use devices due in part to its easy to assemble design, low cost components and environmentally easy to dispose materials without springs, bolts and nuts.

Several embodiments of the invention have thus been described. However, those ordinarily skilled in the art will recognize that the invention is not limited to the embodiments described, but can be practiced with modification and alteration within the spirit and scope of the appended claims that follow.

The invention claimed is:

1. An apparatus for fluid delivery from a flexible container, the apparatus comprising:
    a bottom casing;
    a top casing attached to the bottom casing;
    a wedge member disposed between the bottom casing and the top casing, the wedge member comprising a first edge contactable with an edge of a first block member, and a second edge contactable with an edge of a second block member, the first and second edges of the wedge member forming a curvilinear profile;
    the flexible container disposed between the wedge member and the bottom casing;
    the first and the second block members arranged between the wedge member and the top casing, a narrow end of the wedge member is disposed between the first and second block members; and
    a resilient means coupled to at least one of the first and second block members,
    wherein the resilient means causes the first and second block members to move towards each other by which the wedge member moves towards the bottom casing to squeeze the fluid out of the flexible container.

2. The apparatus of claim 1, wherein the first and second edges of the wedge member form a tapered profile.

3. The apparatus of claim 1, wherein the first and second block members each comprises a knob member engageable to at least one groove on the top casing to guide the movement of the first and second block members.

4. The apparatus of claim 3, wherein the at least one groove penetrates through the top casing and the knob members extend out of the top casing through the at least one groove.

5. The apparatus of claim 1, wherein the resilient means in the extended position is retractable to a position that is less extended than the extended position.

6. The apparatus of claim 1, wherein each of the first and second block members includes a groove and the resilient means includes an elastic band that sits snugly in the grooves.

7. The apparatus of claim 1, further comprising a plate attached to the wedge member and disposed between the wedge member and the bottom casing.

8. The apparatus of claim 1, wherein an inner surface of the top casing includes ribs to reduce a contact area between the first and second block members.

9. The apparatus of claim 1, wherein an inner surface of the top casing is corrugated to reduce a contact area between the first and second block members.

10. A kit of parts for assembling a pump apparatus for fluid delivery, the kit of parts comprising:
    a bottom casing;
    a plate having a first and a second surface;
    at least a first and a second block member;
    a wedge member attachable to the second surface of the plate, the wedge member comprising a first edge contactable with an edge of the first block member, and a second edge contactable with an edge of the second block member, the first and second edges of the wedge member forming a curvilinear profile;
    a resilient means for coupling the first and second block members, the first and second block members moveable to define at least an opening for receiving the wedge member; and
    a top casing attachable to the bottom casing, the top casing for supporting the first and second block members when attached to the bottom casing.

11. The kit of parts of claim 10, wherein the first and second edges of the wedge member form a tapered profile.

12. The kit of parts of claim 10, wherein the first and second block members each comprises a knob member engageable to at least one groove on the top casing to guide the movement of the first and second block members.

13. The kit of parts of claim 10, further comprising a bag for containing fluid, the bag contactable to the bottom casing and the first surface of the plate.

* * * * *